United States Patent [19]
Minkkinen et al.

[11] Patent Number: 5,491,274
[45] Date of Patent: Feb. 13, 1996

[54] PROCESS AND DEVICE FOR CATALYTIC DEHYDROGENATION OF A $C_{2+}$ PARAFFINIC CHARGE COMPRISING A SELF-COOLING SYSTEM

[75] Inventors: Ari Minkkinen, Saint Nom la Breteche; Jean-Pierre Burzynski, Sainte-Foy-les Lyon, both of France

[73] Assignee: Institut Francais du Petrole, Rueil Malmaison, France

[21] Appl. No.: 148,267

[22] Filed: Nov. 8, 1993

[30]  Foreign Application Priority Data

Nov. 6, 1992 [FR] France ................. 92 13515

[51] Int. Cl.⁶ ................................ C07C 5/333
[52] U.S. Cl. ................ 585/655; 585/324; 585/654
[58] Field of Search ............... 585/654, 655, 585/633, 324

[56]  References Cited

U.S. PATENT DOCUMENTS

| | | | |
|---|---|---|---|
| 4,381,417 | 4/1983 | Vora et al. | 585/655 |
| 4,381,418 | 4/1983 | Gewartowski et al. | 585/655 |
| 4,663,493 | 5/1987 | Vora et al. | 585/655 |
| 4,695,662 | 9/1987 | Vora | 585/324 |
| 5,214,225 | 5/1993 | Hall et al. | 585/654 |

FOREIGN PATENT DOCUMENTS 0596800  5/1994  European Pat. Off.

*Primary Examiner*—Ponnathapura Achutamurthy
*Attorney, Agent, or Firm*—Millen, White, Zelano & Branigan

[57]  ABSTRACT

A process and a device for catalytic dehydrogenation of a $C_{2+}$ paraffinic cut with an improved system for cooling the effluent is applicable, for example, to the synthesis of methyl tert-butyl ether. Liquid charge 12 is evaporated in the calandria of a heat exchanger 13 in the optional presence of at least one part recycled hydrogen 15, then optionally compressed in a compressor 14 before being preheated in an exchanger 41 by effluent 1 and introduced into a dehydrogenation reactor 40. The effluent cooled in the tubes of exchanger 13 can be mixed with a cryogenic phase 17 resulting from the isentropic expansion of a hydrogen-rich phase separated in a separator 8, the hydrogen optionally being recycled to the calandria of the heat exchanger. The olefins recovered with the unconverted paraffins are stabilized in a column 20.

12 Claims, 1 Drawing Sheet

PROCESS AND DEVICE FOR CATALYTIC DEHYDROGENATION OF A $C_{2+}$ PARAFFINIC CHARGE COMPRISING A SELF-COOLING SYSTEM

CROSS-REFERENCE TO RELATED APPLICATION

This application is related to a concurrently filed application Ser. No. 08/148,274, entitled PROCESS AND DEVICE FOR CATALYTIC DEHYDROGENATION OF $C_{2+}$ PARAFFIN CHARGE COMPRISING MEANS FOR INHIBITING THE EFFECT OF WATER IN THE EFFLUENT (Attorney Docket No. PET 1189), based on French Application No. 92/13.516, filed Nov. 6, 1992, by Ari Minkkinen, Jean Pierre Burzynski, and Joseph Larue.

BACKGROUND OF THE INVENTION

This invention relates to a process and associated apparatus for the catalytic dehydrogenation of a $C_{2+}$ paraffinic hydrocarbon charge. It relates more specifically to the separation of a hydrogen-rich gas and a hydrocarbon liquid phase from effluents of a low pressure reaction containing the hydrogen intended to be recycled.

The prior art is illustrated by U.S. Pat. Nos. 4,381,417; 4,381,418; and U.S. Pat. No. 4,663,493.

It is known that a number of industrial processes using low pressure catalytic reactions operate in a hydrogen environment in which the partial pressure of hydrogen is maintained by recycling of a hydrogen-rich gas contained in a reaction effluent and which has been separated from the hydrocarbons.

This is the case, in particular, for the catalytic dehydrogenation process of LPG's containing propane, butane, and isobutanes to produce monoolefins which serve as intermediates for the production of fuels with high octane number. In the case of the dehydrogenation of isobutane, the isobutene produced can react with methanol to produce methyl tert-butyl ether, an additive that can be used in gasolines.

The prior art is also illustrated by U.S. Pat. Nos. 4,381,418 and 4,381,417. In such processes, the reaction is performed in a continuously regenerated catalytic reactor operating at very low pressure (slightly greater than the atmospheric pressure or under vacuum) and at temperatures of 500°–600° C.

The combination of the recycled hydrogen and the produced hydrogen provide a sufficient partial pressure of hydrogen so as to inhibit the formation of coke, thereby maintaining the stability of the catalyst. Thus, a satisfactory conversion at a higher range of temperatures up to, for example, about 600° C., can be achieved. Generally, the low pressure effluent discharged from the dehydrogenation reaction zone is first cooled by heat exchange against the gaseous charge and then with water at a suitable temperature. The vapor pressure of the effluent is then raised in conventional compression equipment to a higher pressure, which makes possible the separation of the hydrogen and the hydrocarbon compounds of the effluent.

The separation of the hydrogen from the hydrocarbons in the effluent is performed, in general, at a pressure higher than that prevailing in the reaction zone. Moreover, to condense the hydrocarbons in the gas mixture constituting the effluent and containing hydrogen, it is necessary to cool the gas mixture to a temperature lower than that which conventional cumbersome air or water heat exchangers can achieve.

Other recommended external cooling systems employ propane or propylene cycles, but they are expensive and consume large amounts of energy.

Furthermore, since cooling below 0° C. is required for the separation of the hydrogen and hydrocarbon compounds, the water present in the compressed effluent must be removed sufficiently so that the residual water does not freeze, thereby avoiding fouling of the cooling equipment. For this purpose, 3 Å(1 Å= $1\times10^{-10}$ m) molecular sieves are used to remove the water of the effluent before the cooling step.

SUMMARY OF THE INVENTION

An object of the invention is to eliminate the disadvantages mentioned above and more particularly to achieve as complete a separation as possible between the recycling hydrogen and the olefinic hydrocarbon compounds of the effluent so as to result in a high conversion rate.

Another object of the invention is to provide a cooling circuit of the completely self-cooled compressed effluent eliminating the necessity for external cooling cycles.

Another object of the invention is to provide a reactor operating under the lowest possible pressure in direct connection with downstream pieces of equipment with slight pressure drop producing the lowest possible backpressure, which contributes to increasing the conversion rate of the unit.

Upon further study of the specification and appended claims, further objects and advantages of this invention will become apparent to those skilled in the art.

Generally, the invention relates to a process for the catalytic dehydrogenation of a $C_{2+}$ paraffinic hydrocarbon charge comprising a dehydrogenation step in a dehydrogenation zone, said charge being in the gas phase in the optional presence of hydrogen, said step producing a dehydrogenation effluent comprising water, hydrogen, olefinic hydrocarbons, and unconverted paraffinic hydrocarbons; at least one step of cooling the effluent in an indirect cooling zone with said charge; a step of compressing the effluent at a suitable pressure; a step of eliminating water from the compressed effluent; a step of cooling the compressed effluent in a dual-chamber heat exchanger; a step of separating the cooled effluent; and a step of recovering, on the one hand, a hydrogen-rich vapor phase and, on the other hand, a hydrocarbon liquid phase comprising the olefinic hydrocarbons and the unconverted hydrocarbons.

More specifically, the cooling step comprises the introduction of the hydrocarbon charge in the liquid phase into a first chamber ("side") of said heat exchanger, the heat exchanger being designed to evaporate said charge in the first chamber and to cool, by indirect exchange, the compressed effluent in the second chamber ("side"), the process further being characterized in that the evaporated charge is recovered from the first chamber of the heat exchanger that is introduced into the dehydrogenation zone.

Before being cooled, the effluent is generally compressed at a suitable pressure to be able to recover during the steps of cooling and separation at least 95%, and preferably at least 98% of isobutene in the effluent, if it involves a $C_4$ cut.

According to a first variant of the process, it is possible to recycle at least one part of the hydrogen-rich phase in the first chamber of the heat exchanger where it is put in contact with the liquid bath, and recover the evaporated charge containing the hydrogen that is introduced into the dehydrogenation zone.

According to another variant of the process, it is possible to expand isentropically by suitable expansion means the hydrogen-rich vapor phase so as to separate a hydrocarbon residual condensate and hydrogen, it is possible to recycle at least partly the hydrogen thus separated in the first chamber of the heat exchanger where it is put in contact with the liquid charge and it is possible to recover the evaporated charge and the hydrogen that are introduced into the dehydrogenation zone.

According to a characteristic of this last variant, the hydrocarbon residual condensate resulting from the separation at low pressure of the hydrogen-rich vapor phase and therefore at very low temperature can be mixed with the effluent of the second chamber of the heat exchanger to reduce its temperature by several additional degrees (2° C. to 10° C., for example).

According to another characteristic of the process, it is possible advantageously to reduce the temperature of the effluent in the heat exchanger by compressing the evaporated charge with or without the recycled hydrogen leaving the first chamber of the heat exchanger. The pressure inside the first chamber of the heat exchanger is thereby reduced to 0.2 to 3 absolute bars. This step of reducing pressure in the first chamber combined with the cooling by the evaporated charge and the hydrogen is all the more advantageous when the charge contains heavy hydrocarbons, for example, $C_5$-hydrocarbons.

Furthermore, these additional cooling steps make it possible to avoid high compression levels of the effluent upstream from the step of eliminating water and therefore to minimize the costs of investment and of operation. It is, therefore, possible to combine advantageously the levels of pressure and temperature as well as the amount of hydrogen recycled in the first chamber of the heat exchanger to obtain the temperature required for separation of the phases at lowest possible cost.

Generally, the charge can comprise paraffinic hydrocarbons with 3, 4, and/or 5 carbon atoms. More specifically, it can comprise isobutane. Furthermore, it can consist of a fresh charge, as well as recycled, unconverted, paraffinic hydrocarbons.

The operating conditions of the process are generally the following:

Dehydrogenation Step

Volume space velocity (in relation to the liquid charge) =0.5 to 20 $h^{-1}$, preferably 1.5 to 6 $h^{-1}$.
P= 0.1 to 10 absolute bars, preferably 1 to 4 bars (1 bar= $10^5$ sPa)
T= 400°–800° C., preferably 500°–600° C.

Step of Cooling the Effluent at the Output of the Reactor by the Evaporated Charge with or without Hydrogen T°=50°–150° C., preferably 90°–110° C.

Step of Compressing the Effluent

P= 3 to 35 absolute bars and preferably 10 to 18 bars.
Temperature at the output, preferably 100°–150° C.

Cooling Step: without Compression Downstream

—Chamber of cold fluid (first chamber)
P=1.2–5 absolute bars, preferably 1.5–2.5 bars
T= –5° C. to –90° C., preferably –15° C. to –40° C.
Molar ratio $H_2$ to charge=0–5, preferably 0.5–2.
—Chamber for effluent (second chamber)
P= 3–35 bars, preferably 8 to 12 absolute bars
T=0° C. to –85° C.; preferably –20° C. to –40° C.

Step of Separating the Hydrocarbons of the Effluent from the Hydrogen-rich Vapor Phase P=3–35 bars, preferably 8–12 absolute bars
T=0° C. to –100° C., preferably –20° C. to –40° C.

Step of Isentropic Expansion of the Hydrogen-rich Vapor Phase

P= 1.2 to 5 absolute bars, preferably 2 to 3 bars
T= –50° C. to –100° C., preferably –75° C. to –85° C.

Step of Compressing the Evaporated Charge Downstream from the Cold Chamber of the Heat Exchanger Pressure in the cold chamber of 0.2 to 3 absolute bars
Temperature of the charge at the output of the compressor 0°–50° C., preferably 10° C. to 20° C.

According to another characteristic of the process, it is possible to compress the other part of the hydrogen which has been expanded and separated from the hydrogen-rich vapor phase at a pressure of 5 to 10 absolute bars delivered by a compressor set in motion by the means for expanding the hydrogen-rich vapor phase.

The invention also relates to a catalytic dehydrogenation unit comprising in combination a dehydrogenation reactor (40), means for feeding a hydrocarbon gas charge and optionally means for feeding hydrogen, connected to a reactor input (40), at least one means (41) for cooling an effluent connected to an output of the reactor, means (6) for compressing the effluent connected to the cooling means, means (10) for eliminating water contained in the effluent connected to the compression means, means (13) for cooling the compressed effluent connected to the means for eliminating water, means (8) for separating the cooled effluent connected to the cooling means, means for recovering a hydrogen-rich phase (22) and means for recovering an olefinic hydrocarbon-rich phase (18), said unit being characterized in that the cooling means comprise a dual-chamber indirect heat exchanger (13), a first chamber having an input connected to means (12) for feeding the liquid charge and an output connected to cooling means (41), said heat exchanger (13) being suited to evaporate the charge in said first chamber, to evacuate by said output and to cool the effluent by indirect heat exchange in the second chamber, said second chamber being connected to separating means (8).

According to a first variant of the unit, the first chamber of heat exchanger (13) comprises another input connected to means for recovering a hydrogen-rich phase (22) and means suited to mixing the hydrogen and the charge.

According to a second variant of the unit, the means for recovering a hydrogen-rich phase (22) comprise expansion means (23) connected to a phase separator (27), said phase separator having a first output of hydrogen gas connected to the other input of the first chamber of the heat exchanger.

By the process according to the invention, excellent results in terms of separation and conversion have been obtained. The use of the liquid charge as a cooling source optionally in contact with the hydrogen eliminates the need for external heat exchangers, which makes the process economical investment wise and energywise. In addition, less fluid is necessary in the transfer lines, which reduces the backpressure of the system.

BRIEF DESCRIPTION OF THE DRAWINGS

The invention will be better understood on viewing the attached figure, which is a schematic flowsheet of a preferred comprehensive embodiment of the dehydrogenation process based on a charge containing 93% isobutane.

DETAILED DESCRIPTION OF THE PREFERRED EMBODIMENTS

Figure 1:
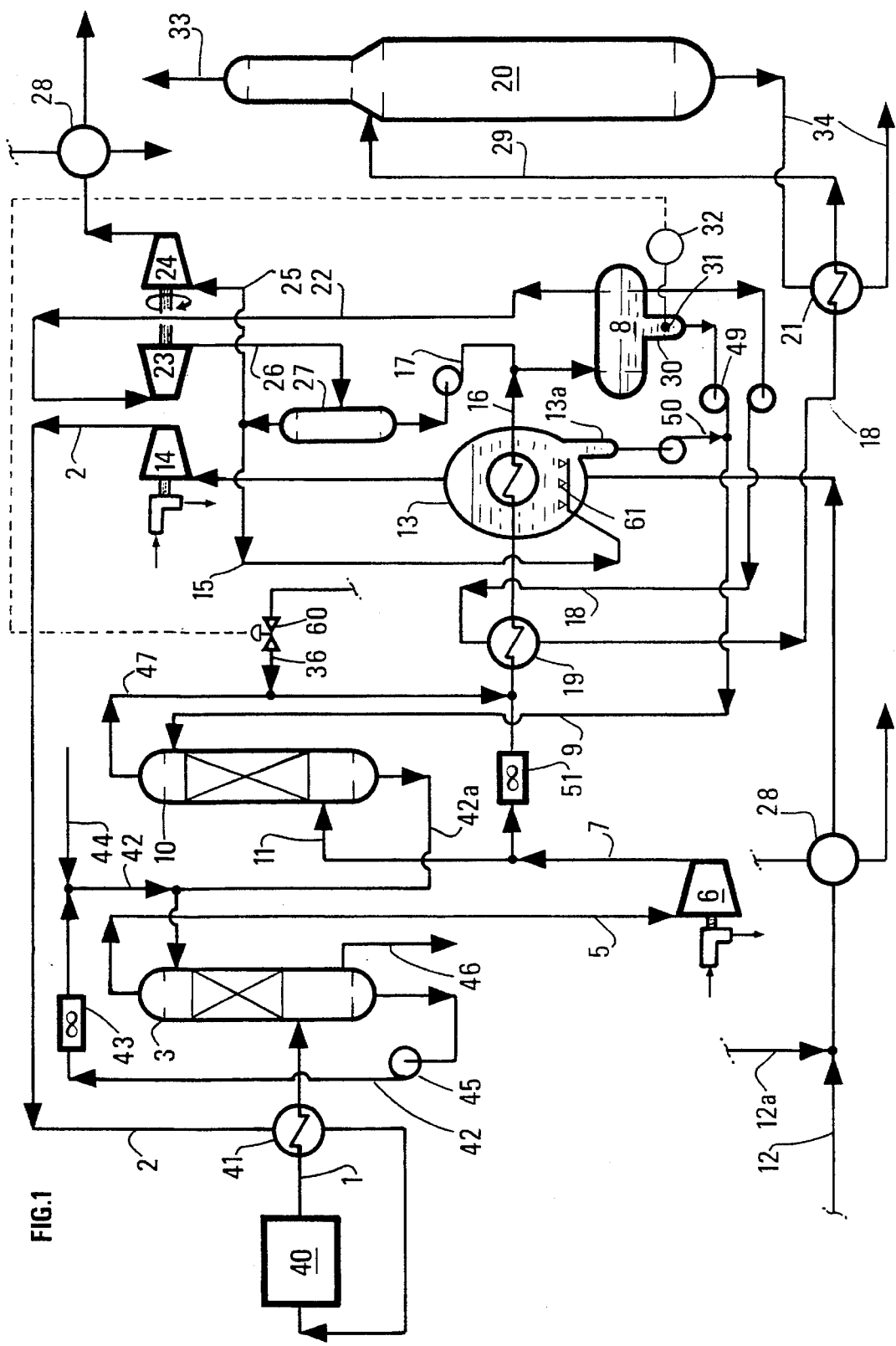

The isobutane charge 2, in gas form, and hydrogen, after having been preheated to a suitable temperature by indirect exchange in a plate heat exchanger 41, with only a slight pressure drop, are introduced into a catalytic dehydrogenation reactor 40 operating at low pressure (1.5 to 1.8 absolute bars) and at high temperature 580°–600° C. The effluent discharged via a line 1 is cooled by indirect exchange in this plate exchanger, then in another heat exchanger 3, again with only a slight pressure drop, using water as a cooling fluid. After being passed into a safety or surge vessel 4, the cooled but still superheated effluent is fed by a line 5 into the suction side of a centrifugal compression system 6 capable of raising the pressure considerably above atmospheric pressure.

Compression system 6 raises the pressure of the reaction effluent to a value such that an effective separation of a liquid hydrocarbon phase from a hydrogen-rich gas phase becomes possible at a temperature generally less than 0° C. In the case of the dehydrogenation of the isobutane, a pressure of 13 to 18 bars is quite suitable. The energy requirements of the compression system can be provided by a gas turbine, a steam turbine or an electric motor.

A conduit 7 is connected to the output of compressor 6 and guides the compressed effluent into heat exchanger 51, where the effluent is cooled. The cooled compressed effluent is then passed through at least one bed 10 of a 3 angstrom molecular sieve (1 angstrom=1×10$^{-10}$ m) to remove approximately all the water and which operates interchangeably with at least one other bed according to a conventional cyclic mode of adsorption and regeneration. A line 11 recovers the compressed and dehydrated effluent at the bottom of the bed and guides it through a first heat exchanger 19, then through a second heat exchanger 13 provided with tubes and with calandria (a vessel part of an evaporator provided with heating means, e.g., tubes, for indirectly heating and evaporating said liquid in the vessel) to cool the effluent by indirect exchange.

In fact, isobutane charge that is fresh or unconverted, thus recycled, is brought by a line 12 in the liquid phase into the calandria of exchanger 13. Fouling due to the presence of water can be inhibited by adding methanol 42 into line 12. This liquid phase, evaporated by the heat from the tubes, is mixed with at least one part of recycled hydrogen brought in by a line 15, thereby reducing the boiling temperature of the liquid phase at a given pressure. This hydrogen is introduced at the lower part of the calandria by means of perforated tubes 61, for example, suited to promote the contact of hydrogen with said liquid phase approximately throughout the entire space occupied by the latter. Under these conditions, the liquid phase in the calandria is used as coolant. A gas phase is recovered in the upper part of the calandria, comprising evaporated isobutane and hydrogen that is recycled and evacuated by a line 2 by means of a compressor 14 in the direction of plate heat exchanger 41 so as to cool the effluent before reaching the reactor 40.

In lower part 13a of the calandria, it is possible to recover a condensate of methanol and water which can be distilled in the MTBE synthesis unit, downstream.

The pressure inside the calandria of heat exchanger 13 is maintained so that the evaporating temperature will be sufficient to cool the effluent. The evaporation pressure is kept at a suitable level by single-stage, variable speed compressor 14, which has its input connected directly to the calandria.

To obtain an advantageous range of temperatures of the effluent of −25° C. to −10° C., the pressure in the calandria is kept at about 2 absolute bars. By compressor 14, the charge in the vapor phase (isobutane and hydrogen) is compressed to a pressure of 3 to 4 absolute bars and passed toward the input of the dehydrogenation reactor.

The effluent cooled in the tubes of heat exchanger 13 goes out through a line 16 at a temperature of about −20° C. to −25° C., for example, and is directed toward a phase separator 8. At the head of the separator, through line 22, there is withdrawn a vapor phase containing mostly hydrogen and a small proportion of hydrocarbons, and said vapor phase is passed into a turbo-pressure reducing device 23, e.g., an expansion turbine, where it is expanded at constant entropy at a pressure, for example, from 15 bars to a pressure of about 2.5 bars. At the output of turbo-pressure reducing device 23, the temperature in line 26 typically drops, from about −25° C. to about −85° C., which causes the condensation of a "cryogenic" hydrocarbon liquid phase which is separated from the hydrogen in a phase separation chamber 27. This liquid phase is recovered at the bottom of chamber 27 by a line 17 and mixed with the cooled effluent exiting from cooling heat exchanger 13, at a point upstream from the input of phase separator 8. This direct contact optionally promoted by suitable means for mixing contributes to cooling, by direct heat exchange, of the compressed effluent by about an additional 2°–10° C.

At the upper part of separation chamber 27, a hydrogen gas phase (more than 98% molar) of hydrogen is recovered, which is divided to form a hydrogen stream intended to be recycled partly by a line 15 and sent first of all into the calandria of cooling heat exchanger 13 to evaporate the liquid charge of isobutane. The other part of the hydrogen stream is directed by a line 25 to a compressor 24 coupled to and driven by turbo-pressure reducing device 23. This hydrogen stream compressed at about 10 bars and at a temperature of −30° C. can be reheated in a heat exchanger 28 placed on line 12 downstream from the addition 42 of methanol, by direct exchange with the liquid charge of isobutane, and can thereby contribute to supercooling the charge before its evaporation.

At the bottom of the phase separator 8, a hydrocarbon liquid phase at about −25° C. and about 15 absolute bars, containing at least 95% isobutene is recovered in line 18 and is used to cool the effluent in a heat exchanger 19 before the effluent is passed into cooling heat exchanger 13. The hydrocarbon liquid phase is further reheated in another heat exchanger 21 before being introduced into a stabilization column 20 delivering at the head by a line 33 a gaseous fuel and at the bottom by a line 35 isobutene and unconverted isobutane which contribute to the thermal exchange in exchanger 21 and which are sent to an MTBE-forming unit (not shown).

It is possible to control the temperature of the phase separator 8 by adjusting the pressure level in the calandria of exchanger 13 either by a valve on line 2 at the output of the exchanger, or by the control of the rpm of compressor 14.

The entire disclosures of all applications, patents, and publications, cited above and below, and of corresponding French Application No. 92/13.515, filed Nov. 6, 1992, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for catalytic dehydrogenation of a $C_{2+}$ paraffinic hydrocarbon charge comprising:

a) dehydrogenating in a catalytic dehydrogenating zone under dehydrogenation conditions said charge in the gas phase in the presence of hydrogen to provide a dehydrogenation effluent comprising water, hydrogen, at least one olefinic hydrocarbon and at least one unconverted paraffinic hydrocarbon, b) one or more steps of cooling the dehydrogenation effluent in an indirect cooling zone with said charge before it is introduced into the dehydrogenation zone, c) compressing the thus-cooled effluent, d) eliminating water from the compressed effluent, e) cooling the compressed effluent in a dual-chamber heat exchanger, f) separating the thus-cooled effluent into a hydrogen-rich vapor phase and a hydrocarbon liquid phase comprising at least one olefinic hydrocarbon and unconverted hydrocarbons, and g) isentropically expanding the hydrogen-rich vapor phase to separate a hydrocarbon residual condensate, which is mixed with the cooled effluent from the dual-chamber heat exchanger, and hydrogen, at least a part of which is directly recycled to a first chamber of said dual-chamber heat exchanger and, therein, contacting said hydrogen with the charge in the liquid phase in said first chamber, wherein, for the cooling in the dual-chamber heat exchanger, the charge in the liquid phase, before being introduced to the dehydrogenation zone, is introduced into a first chamber of said dual-chamber heat exchanger, said first chamber being of sufficient volume to allow vaporization of the charge therein, and the compressed effluent is introduced into a second chamber of said dual-chamber heat exchanger such that the charge is evaporated and recovered from the first chamber and passed to the dehydrogenation zone, and the compressed effluent is cooled by indirect heat exchange.

2. Process according to claim 1, wherein said charge comprises paraffinic hydrocarbons with 3, 4 and/or 5 carbon atoms.

3. Process according to claim 1, wherein said charge essentially comprises isobutane.

4. Process according to claim 1, wherein the step of compressing the effluent is performed at a pressure of 3 to 35 absolute bars.

5. Process according to claim 1, wherein the temperature in the first chamber of the heat exchanger is −5° to −90° C. under a pressure of 1.2 to 5.0 absolute bars.

6. Process according to claim 1, wherein the hydrogen-rich vapor phase is expanded at a pressure of 1.2 to 5.0 absolute bars under a temperature of −50° to −100° C.

7. Process according to claim 1, wherein the charge optionally containing hydrogen is compressed, going out of the first chamber of the heat exchanger so that the pressure in said first chamber of the heat exchanger where the charge is evaporated is 0.2 to 3 bars, and the compressed, evaporated charge is sent to the dehydrogenation zone via the cooling zone.

8. Process according to one of claims 1 to 7, wherein the other part of the hydrogen separated from the condensate is compressed at a pressure of 5 to 10 absolute bars by a compressor set in motion by the expansion means to cool said liquid charge.

9. The process of claim 8, wherein in step g), at least a part of the hydrogen from the hydrogen-rich vapor phase recycled to the first chamber of said dual-chamber heat exchanger is introduced into the lower part of said first chamber.

10. The process of claim 8, wherein in step g), at least a part of the hydrogen from the hydrogen-rich vapor phase recycled to the first chamber of said dual-chamber heat exchanger is introduced into said first chamber through perforated tubes.

11. The process of claim 8, wherein the dual-chamber heat exchanger is in the form of a calandria as the first chamber surrounding one or more tubes as the second chamber.

12. The process of claim 1, wherein the charge recovered from the first chamber of the dual chamber heat exchanger is compressed before being introduced to the dehydrogenation zone.

* * * * *